United States Patent [19]

Edwards et al.

[11] 4,418,315
[45] Nov. 29, 1983

[54] METHOD FOR EFFECTING A SURFACE EXAMINATION OF COATED COMPONENTS

[75] Inventors: Lawrence J. Edwards, Suffield; John P. Lareau, Granby, both of Conn.

[73] Assignee: Combustion Engineering, Inc., Windsor, Conn.

[21] Appl. No.: 266,397

[22] Filed: May 22, 1981

[51] Int. Cl.$^3$ ............................................. G01R 35/00
[52] U.S. Cl. .................................................. 324/202
[58] Field of Search .................. 324/202, 262; 73/1 R

[56] References Cited

U.S. PATENT DOCUMENTS 2,862,178  11/1958  Moore ............................... 324/202

FOREIGN PATENT DOCUMENTS 635437  11/1978  U.S.S.R. ............................. 324/202

Primary Examiner—Gerard R. Strecker
Assistant Examiner—Walter E. Snow
Attorney, Agent, or Firm—Arthur E. Fournier, Jr.

[57] ABSTRACT

A method of effecting an examination by eddy current means (24) of the surface of a coated component (58) for cracks having at least a preset minimal dimension. The subject method can be used to detect such cracks in the surface of metal components (58) that are coated or covered with a nonmetallic material. Further, through the use of the subject method such cracks are detectable without necessitating the removal of the nonmetallic coating or covering from the surface of the metal component (58). The subject method encompasses the steps of establishing calibration readings for cracks of the desired dimension utilizing the eddy current means (24) with which the desired surface examination of the given component (58) is to be effected, performing a preexamination validation of the operativeness of the eddy current means (24), and conducting with the eddy current means (24) the surface examination of the given metal component (58) that is coated or covered with a nonmetallic material.

6 Claims, 3 Drawing Figures

METHOD FOR EFFECTING A SURFACE EXAMINATION OF COATED COMPONENTS

BACKGROUND OF THE INVENTION

This invention relates to the examination of articles for defects, and more specifically to a method of conducting an eddy current surface examination of a metal component that is coated or covered with a nonmetallic material for purposes of detecting therein, without the necessity of removing the coating or covering from the component, cracks that are of at least a preestablished minimal dimension.

There are known to exist many instances wherein it is desirable and/or necessary to effect a surface examination of an operating component. Notwithstanding the number of such instances and the differences that exist therebetween, in general one finds that the reason for conducting such a surface examination is associated in some manner with the need to determine the relative operating condition of the component in question. That is, commonly there exists a need to ensure the operability of the component preparatory to its being placed in service and/or the need periodically to verify that the component is still in good working order. To this end, it is not uncommon to find that standards have been promulgated in this regard for various kinds of operating components. Namely, these standards which have been promulgated serve to establish the nature and/or extent of the surface defects which will be deemed to render a particular type of operating component unserviceable.

By way of exemplification and not limitation, reference is had here to rotary members, as being representative, generally, of one such form of component. Further, one specific type of rotary member to which reference may be made in this connection is that of flywheels, and in particular flywheels of the sort, which often are found cooperatively associated with the coolant circulation pump motors that are employed in nuclear steam supply systems. The function which flywheels perform in this type of a nuclear-related application is that of assisting in the accomplishment of coastdown of the coolant circulation pump motors. As such, it is, therefore, important that when the flywheels are needed that they be capable of functioning in their intended manner. To this end, obviously one way of ensuring that the flywheels are in good working order is to periodically conduct an examination of the flywheels for defects. Moreover, rather than depending on compliance with some voluntary schedule of examination of such components, it is known that in a number of instances governmental authorities have promulgated regulations that mandate the performance of such periodic examination with regard to particular components for purposes of effecting a detection of defects therein that could impair the operativeness of the component. This is prticularly true in the case of many of the operating components of a nuclear steam supply system.

With specific regard to flywheels of the sort referred to above, i.e., the large flywheels needed for coastdown in nuclear reactor coolant circulation pump motors, existing governmental regulations require that they undergo surface examination during preservice and at ten year intervals during the life of the nuclear plant in which they are installed. The performance of such a surface examination on such flywheels is rendered more difficult by virtue of the fact that these flywheels are normally painted to provide them with corrosion protection against the high humidity environment to which they are subjected. Thus, for purposes of accomplishing such surface examinations there has existed a need in the past for removing the flywheels from the motors followed by the sand blasting thereof down to the base metal surface to remove the paint therefrom.

Note should be taken here of the fact that in requiring that surface examinations be performed on such flywheels, governmental regulations have not only specified the frequency of such examinations and the nature of the defects which the surface examination was intended to detect, but have also dictated the manner in which the examination is to be performed. Namely, such governmental regulations have heretofore required that the surface examination be conducted in accordance with the procedures that are found set forth in the applicable industrial codes, which have been promulgated governing the performance of surface examination on metal components.

In this regard, until now in order to comply with governmental regulations the surface examination of flywheels of the type being discussed herein has had to be performed by either of two techniques. That is, the only techniques acceptable for use for this purpose have been those of dye penetrant and magnetic particle. Both of these, however, require that the examination be conducted on a clean base metal surface. Accordingly, when the component that is to be examined, as in the case of the subject flywheels, has had a coating or a covering applied thereto, the removal of the latter must first be effected before the dye penetrant or magnetic particle inspection thereof can be had. In the case of flywheels associated with reactor coolant circulation pump motors this has meant that during a refueling or maintenance outage significant time and manpower has had heretofore to be expended in the disassembly of the motors, flywheel removal and subsequent surface preparation for the examination, not to mention the necessity of constructing special facilities for the sand blasting. Presently, this cycle of motor disassembly, flywheel cleaning, examination and reassembly requires about seven days to complete per flywheel exclusive of the time required for evaluation of the examination results. This seven days in turn represents motor downtime as well as radiation exposure time for the workers involved in performing these tasks. As regards motor downtime, recognition must be had of the fact that in order to accomplish the removal of the flywheel, etc., the motor must be sufficiently disassembled such that it cannot readily be placed back in service should a need therefor arise.

In addition to the disadvantages enumerated above that are associated with the use of the techniques of dye penetrant and magnetic particle for purposes of performing surface examinations of metal components, there are also other disadvantages associated with the usage thereof. For example, in the case of the subject flywheel, a surface examination is commonly made at the time of the completion of the manufacture thereof. Thereafter, when the flywheel reaches the site whereat it is to be employed, the flywheel normally would undergo yet another surface examination, i.e., a preservice surface examination. Finally, surface examinations will be conducted periodically on the flywheel after it has been placed in service. To the extent the flywheel for purposes of each of these surface examinations must be disassembled from the motor, and must have removed therefrom the corrosion protective coating that has been applied thereto, the possibility arises that inconsistencies can develop in the results obtained from the surface examination that are occasioned by the treatment to which the flywheel is subject in preparation for the surface examination, rather than being representative of the condition of the flywheel at the time just prior to the commencement of the preparation of the flywheel for examination. Further, such inconsistencies can obviously lead one to arrive at misleading conclusions concerning the operative state of the flywheel. Secondly, in the course of effecting the removal of the corrosion protective coating from the flywheel there is commonly a need to make use of solvents, etc. In addition, paint chips are commonly produced. Such solvents and/or paint chips, etc. can detrimentally affect the performance and/or operation of the motor should they become captured therewithin, particularly in view of the relatively high precision nature of such equipment. A need has thus been shown to exist in the prior art for the development of a new and improved technique that would be operative for purposes of conducting surface examinations on coated metal components, and which would not necessitate for its use the removal of the coating from the metal component. Secondly, such a new and improved technique should be capable of use for purposes of effecting a detection from such surface examination of defects in accordance with the requirements established for such detection by existing governmental regulations. Thirdly, such a new and improved technique must be capable of being accepted under the applicable industrial codes as a technique that is recognized for use for the performance of surface examinations on metal components.

It is, therefore, an object of the present invention to provide a new and improved method for effecting a surface examination of a component.

It is another object of the present invention to provide such a method which is particularly applicable for use for purposes of effecting surface examinations of coated metal components.

It is still another object of the present invention to provide such a method for effecting a surface examination of a coated metal component which does not necessitate the removal of the coating from the component for purposes of effecting the surface examination thereof.

A further object of the present invention is to provide such a method which makes use of eddy current means for purposes of effecting a surface examination of a coated metal component.

A still further object of the present invention is to provide such a method which is capable of being used to effect from a surface examination of a coated metal component the detection of defects in accordance with the requirements established for such detection by existing governmental regulations.

Yet another object of the present invention is to provide such a method for effecting a surface examination of a coated metal component which has achieved acceptance under the applicable industrial codes as a technique that is recognized for use for the performance of such surface examinations.

Yet still another object of the present invention is to provide such a method for effecting a surface examination of a coated metal component which is relatively easy to employ and which enables significant economies of time and manpower to be realized through the use thereof as compared to that required when utilizing prior art techniques.

SUMMARY OF THE INVENTION

In accordance with the present invention there is provided a method employable for purposes of effecting a surface examination of a coated metal component to detect defects in the surface thereof without necessitating the removal of the coating from the component. The subject method includes the steps of providing a calibration block that has a plurality of surface cracks of known given dimensions formed therein and which possesses substantially the same metallurgical characteristics as those possessed by the metal component that is to undergo a surface examination, providing a layer of nonmetallic material having characteristics similar to those of the coating that is applied to the metal component which is to undergo a surface examination, positioning the layer of nonmetallic material in superimposed relation on the calibration block so as to cover the plurality of surface cracks that are provided in the latter, with eddy current means establishing calibration readings from the calibration block with the layer of nonmetallic material positioned in superimposed relation thereon, validating the operativeness of the eddy current means as a preliminary to conducting the surface examination of the coated metal component, performing a surface examination of the coated metal component with the eddy current means, and comparing the readings obtained from the surface examination of the coated metal component with the calibration readings to establish whether cracks of at least a given dimension exist in the surface of the coated metal component.

DESCRIPTION OF A PREFERRED EMBODIMENT

Figure 1:
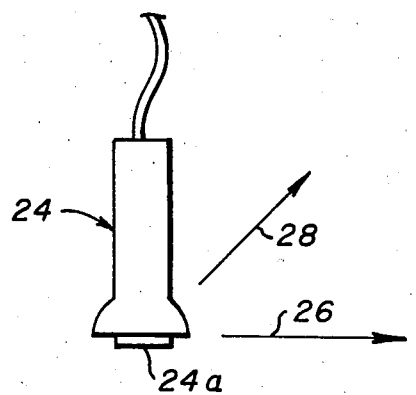
FIG. 1 is an exploded view of the apparatus that is employed for purposes of obtaining calibration readings in accordance with the present invention.
Figure 1:
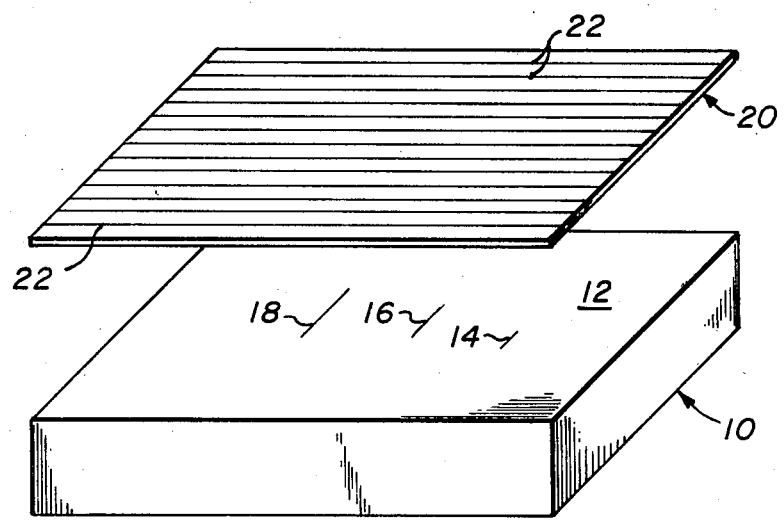

Referring now to the drawing, and more particularly to FIG. 1 thereof, there is depicted therein a calibration block, generally designated by the reference numeral 10. The calibration block 10, which may have any suitable dimensions, is selected so that it has essentially the same metallurgical characteristics as the metal component, the surface of which is to be examined in accordance with the method of the present invention. Further, the calibration block 10 is provided on at least one surface 12 thereof with a plurality of surface cracks, i.e., notches. As depicted in FIG. 1, the latter surface cracks are three in number, i.e., those designated therein by the reference numerals 14, 16 and 18. Each of the cracks 14, 16 and 18 is of a known, given dimension. To this end, one of the surface cracks 14, 16 and 18 preferably embodies the same dimension as that of the minimal dimensioned crack which it is desired to detect when a surface examination is conducted on a coated metal component employing the method of the present invention. By way of exemplification in this regard, the minimal dimension of such a crack may be selected to be 3/16 inch. Accordingly, the crack denoted by the reference numeral 16 in FIG. 1 could be made to have a 3/16 inch dimension, whereas the crack designated by reference numeral 14 in FIG. 1 would be of a known predetermined lesser dimension, and the crack designated in FIG. 1 by reference numeral 18 would be of a known predetermined greater dimension.

Continuing with the description of the structure depicted in FIG. 1, there is also shown therein a layer of nonmetallic material, generally designated by reference numeral 20. The layer 20 is selected so as to have substantially the same characteristics, for eddy current purposes, as the coating or covering with which the metal component that is to undergo a surface examination in accord with the present invention is provided. Further, in accord with the best mode embodiment of the invention, the layer 20 has a multiplicity of equally spaced scribe lines 22 provided on one planar surface thereof for a purpose yet to be described. The spacing between the parallelly extending scribe lines 22 is purposely selected so as to be of a given finite dimension. Finally, with reference to FIG. 1 note is made of the fact that the scribe lines 22 preferably each extend the entire length of the nonmetallic layer 20.

The third structural element appearing in FIG. 1 is that of an eddy current probe, generally designated therein by reference numeral 24. The probe 24 in terms of both its structural form and its mode of operation is of known construction. However, the dimensions, which the probe 24 embodies, is a function of the application in which it is intended to employ the probe 24. In this regard, the considerations upon which the selection of the dimensions of the probe 24 are predicated will be discussed herein subsequently. The probe 24 also, as is known to those in the eddy current art, must balance with the metallic material of which the metal component that is to undergo a surface examination in accordance with the method of the present invention is formed. That is, the electrical characteristics of the probe 24 must be suitably selected so that the probe 24 in terms of its eddy current response will balance when placed in use with the metal of the component that is to have its surface examined therewith. For purposes of better understanding the relationship which exists between the calibration block 10, the layer 20 and the probe 24, a pair of directional arrows 26 and 28 are illustrated in FIG. 1 of the drawing. More specifically, as will be better appreciated from the discussion that follows the directional arrow 26 denotes the direction of movement of the probe 24 relative to the direction in which the scribe lines 22 of the nonmetallic layer 20 extend, whereas the directional arrow 28 designates the index direction of the probe 24 relative to these same scribe lines 22.

Figure 2:
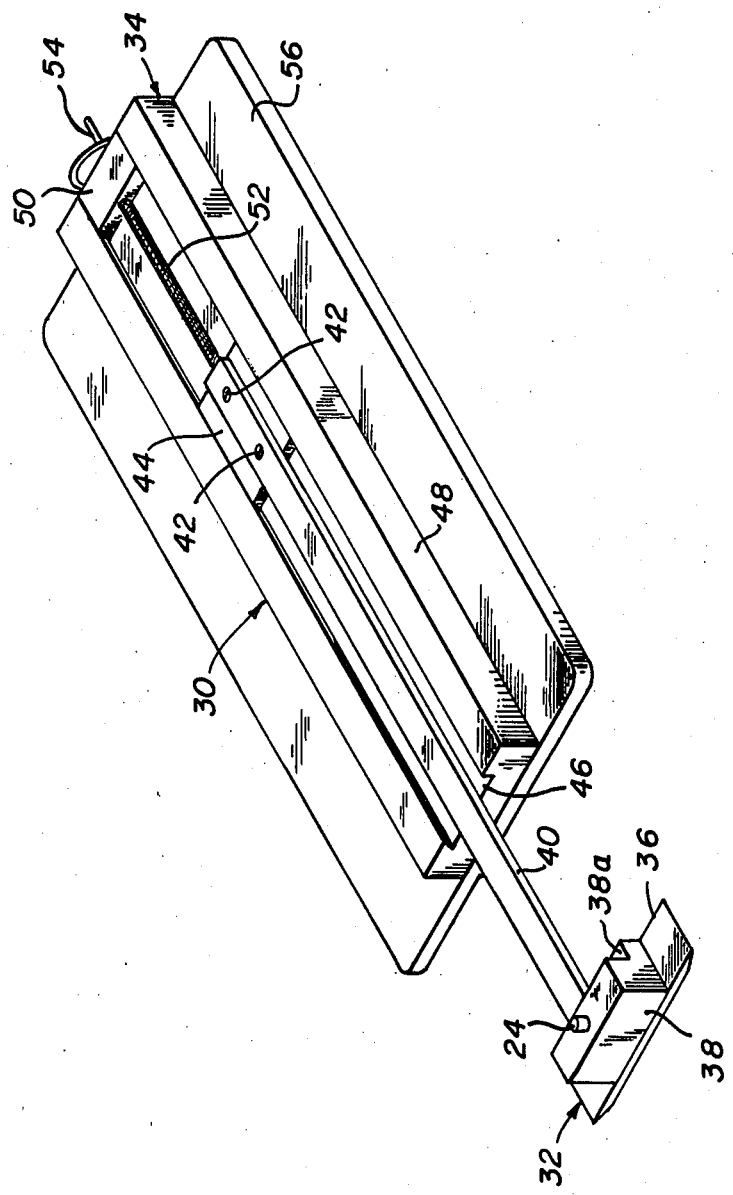
FIG. 2 is a perspective view of the apparatus utilized for purposes of obtaining readings from the surface of a coated metal component during the performance of a surface examination thereof in accordance with the method of the present invention.

In FIG. 2 of the drawing, there is illustrated a probe holder and the indexer means, generally designated therein by the reference numeral 30. The probe holder and indexer means 30 comprises a probe holder portion and an indexer portion, denoted by the reference numerals 32 and 34, respectively. In accord with the best mode embodiment, the probe holder portion 32 preferably includes a sled-like member 36 suitably configured so as to be designed to pass in sliding engagement with the surface of the metal component that is to be examined for defects in accordance with the method of the present invention. Suitably supported in mounted relation on the sled-like member 36 through the use of any appropriate conventional form of mounting means (not shown) is a probe holder 38. The latter probe holder 38 has an opening (not shown) formed therein suitably dimensioned so as to be capable of receiving the probe 24 in inserted relation thereto. Alligned with the aforesaid opening (not shown) is an opening (not shown) that is formed in the sled-like member 36 so as to enable the operating end 24a of the probe 24 to extend therein whereby the aforesaid end 24a of the probe 24 is suitably positioned relative to the surface of the metal component as the sled-like member 36 passes thereover. The probe holder portion 32 is made of a suitable nonmetallic material so as to not interfere with the eddy current signals from the probe 24.

With further regard to the probe holder and indexer means 30 of FIG. 2, the indexer portion 34 thereof is suitably constructed so as to be operative for purposes of effecting with preciseness the indexing relative to a given surface of the probe holder portion 32, and thereby the probe 24 supported thereon for movement therewith. To this end, the indexer portion 34 includes an elongated member 40 having one end thereof suitably affixed through the use of any appropriate form of conventional fastening means (not shown) to the probe holder 38. For this purpose, the probe holder 38 is preferably provided with a ledge-like surface 38a on which the aforesaid one end of the elongated member 40 is designed to rest in fixed relation thereto. The other end of the elongated member 40 is fastened by means of the conventional fasteners 42 to a traveling block 44. The latter traveling block 44 is supported for movement in a suitably dimensioned and configured guideway 46 formed in the frame-like structure 48. To this end, the guideway 46 may, as illustrated in FIG. 2, embody a dovetail-like configuration, which in turn occasions the embodiment by the traveling block 44 of a configuration complementary thereto.

Continuing with the description of the indexer portion 34, the frame-like structure 48 in accord with the illustration thereof in FIG. 2 embodies the form of an elongated, generally rectangular block-like member. One end of the structure 48 is preferably left open to enable the member 40 to extend outwardly therefrom. In addition, the other end of the frame-like structure 48 is preferably closed by a block-like element 50. The latter element 50 has a threaded opening (not shown), preferably centrally located, formed therethrough. An elongated screw thread 52 is received in threaded engagement within the aforesaid threaded opening (not shown). One end of the screw thread 52 is suitably secured to the traveling block 44, while the other end of the screw thread 52, in accord with the illustration of FIG. 2, has a handwheel 54 mounted thereto. Thus, rotation of the handwheel 54 is effective to cause the traveling block 44 to move to and fro within the guideway 46. Such a movement of the traveling block 44 in turn is operative to accomplish the desired indexing of the probe holder portion 32 and thereby the probe 24 relative to a given surface.

Figure 3:
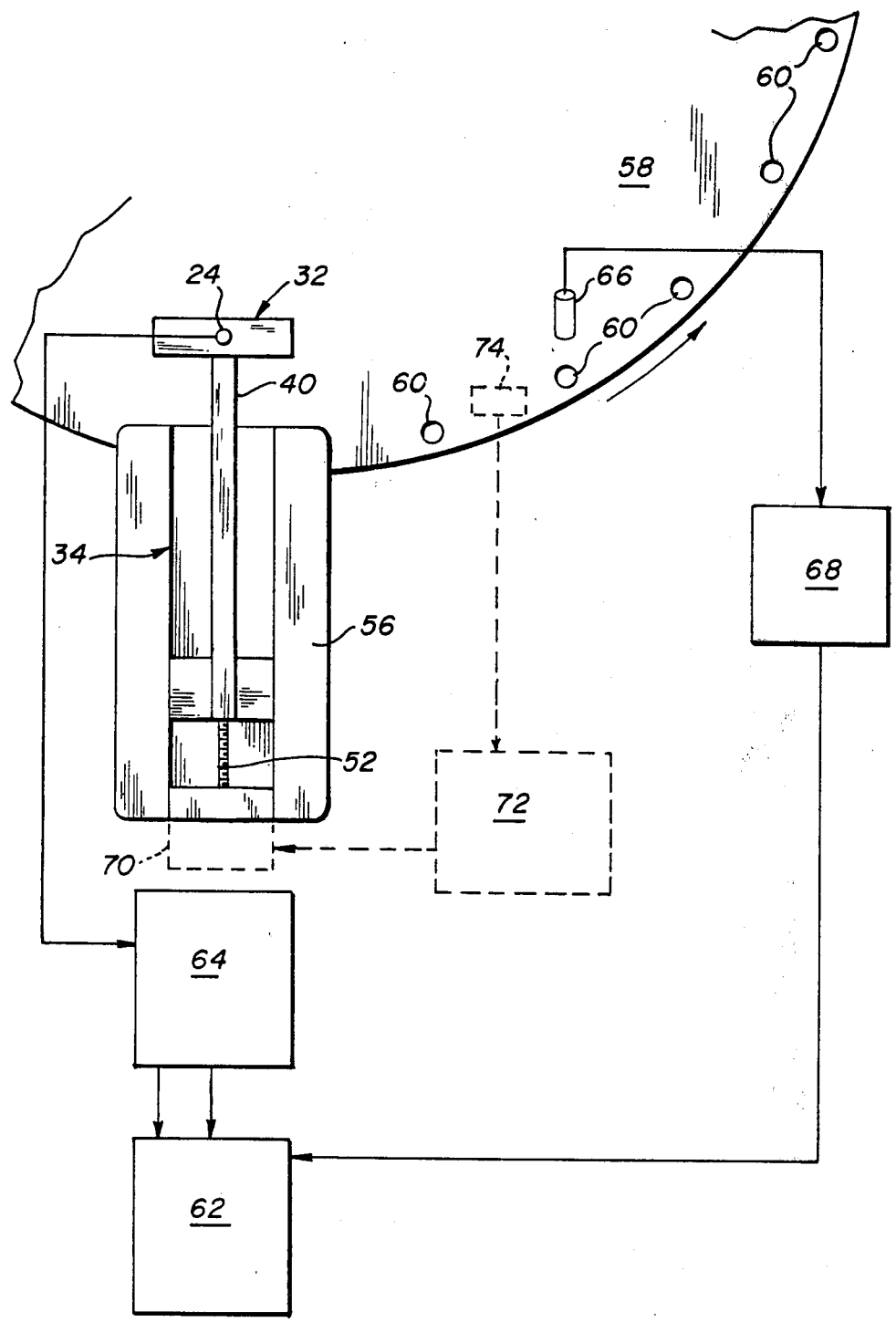
FIG. 3 is a schematic representation of the elements of the eddy current system that is utilized in the performance of a surface examination of a coated metal component in accordance with the method of the present invention.

Completing the description of the structure depicted in FIG. 2 of the drawing, the probe holder and indexer means 30 is preferably suitably mounted in supported relation on a mounting plate 56. The latter mounting plate 56, as will become more fully apparent from a consideration of the illustration of FIG. 3, is employed for purposes of effecting the mounting of the probe holder and indexer means 30 relative to the component which is to undergo a surface examination in accord with the method of the present invention. Finally, although omitted from the illustration thereof, it is to be understood that the probe holder and indexer means 30 could be provided without departing from the essence of the present invention, if so desired, with suitable biasing means operative to effect a biasing of the probe holder portion 32 into engagement with the surface of the component over which the sled-like member 36 is intended to pass.

The structure depicted in FIGS. 1 and 2 of the drawing, which has been described hereinabove, is utilized in the performance of the method of the present invention. Namely, the structure, previously described herein, of FIGS. 1 and 2 forms the elements of an eddy current examination system, which enables through the use thereof cracks to be detected in the surface of metal components that have tightly bound coatings or coverings applied thereto. More specifically, the method of the present invention that makes use of this eddy current examination system is operative to detect such surface cracks in metal components without necessitating the removal from the latter of the coating or covering that is thereon. Moreover, the method of the present invention is operative even though variations in the thickness of such coatings exist. That is, the method of the present invention is capable of accommodating such variations in the thickness of the coatings or coverings applied to the metal components, and even is operative to effect a determination that such variations exist. In accord with one specific application to which the method of the present invention is particularly suited for use, the probe holder and indexer means 30 when employed in accordance with the method of the present invention enables the detection of radial cracks to be had therewith in rotating flywheels. The manner in which this is accomplished will be more fully described hereinafter in connection with a discussion of the showing of FIG. 3 of the drawing.

In accordance with the best mode embodiment of the invention, the coating or covering which is applied to the metal component may be in the form of any tightly bound nonmetallic substance and may have a thickness of up to ten mils. Moreover, the coating or covering may be applied to the metal component by being taped, wrapped or shrink wrapped thereto, or through the use of other special application techniques which will produce a coating or covering of relatively uniform thickness.

One of the various steps in the performance of the method of the present invention is that of calibration. To accomplish the step of calibration, the three components shown in FIG. 1 of the drawing are utilized. Namely, first a piece of metal similar to the component that is to be tested is fabricated to provide a calibration block such as that shown at 10 in FIG. 1. During the fabrication of the calibration block 10, a plurality of surface cracks, i.e., notches are provided in a surface thereof, such as those shown at 14, 16 and 18 in FIG. 1. These cracks 14, 16 and 18 may be provided in the calibration block 10 by means of any conventional machining technique suitable for use for this purpose, e.g., electrical discharge machining. Next, there is provided a layer, i.e., film, 20 of nonmetallic material which may be in the form of a tape, a plastic sheet, etc., that has substantially the same thickness as the coating or covering borne by the component that is to be tested. The layer 20 is positioned in superimposed relation over the surface of the calibration block 10 that has the cracks 14, 16 and 18 formed therein. Lastly, an eddy current probe, e.g., the probe 24 in FIG. 1, is selected for use. The probe 24 is suitably dimensioned so that the layer 20 may be traversed thereby in an acceptable period of time, while concomitantly the sensitivity of the probe 24 remains such that acceptable readings may be generated thereby during the passage thereof over the surface cracks 14, 16 and 18 with which the calibration block 10 is provided. Further, the probe 24 that is selected for use in this connection must be suitably balanced with the metal from which the calibration block 10 is formed. Reference has previously been had herein to the need for such balancing. The purpose in having the eddy current probe 24 pass over the layer 20 in engaging relation therewith while generating a series of calibration readings, i.e., sensings, occasioned by the presence of the crack-like notches 14, 16 and 18 in the calibration block 10 is to effect a simulation of the lift off, i.e., separation between the probe and the component which will be encountered on the actual component as a consequence of the existence thereon of a coating or covering.

In accord with the best mode embodiment of the invention, the layer 20 preferably has a plurality of very accurately positioned scribe lines 22 provided thereon. The function thereof is to enable the operator to move the eddy current probe 24 in a traversing pattern over the surface of the layer 20, and thereby concomitantly over the surface of the calibration block 10. By following this procedure, the operator is assured that the entire surface area of the calibration block 10 will be traversed by the probe 24. The spacing between the scribe lines 22 in accord with the best mode embodiment of the invention is selected such that any crack having the minimal dimension that it is desired to have detected by the probe 24 will generate a signal when the probe 24 is moved along each of two adjoining ones of the multiplicity of scribe lines 22. Such a practice ensures that during the surface examination of the component that is to be examined, any flaw that may be present in the surface thereof will not be missed due to some random initial placement of the probe 24 on the component. Further to this point, the spacing of the scribe lines 22 is preferably selected so that a crack of the desired minimal detectable dimension will produce a signal of at least fifty percent of the signal produced by the entire crack as the probe 24 is moved along the scribe line 22 that is located in superimposed relation over the crack producing the aforesaid signal.

Once the step of calibration has been accomplished, an inspection can be had of the surface of a given metal component. Normally, however, it is desirable that the operativeness of the eddy current probe 24 be verified preparatory to the commencement of the inspection of the given metal component. There are a number of reasons for doing this. One of these is that the calibration readings obtained from the calibration block 10 commonly will be produced at a site which is different from that whereat the metal component which is to be tested is located. Another reason is that there may exist a need to employ an eddy current probe 24 for purposes of performing the surface examination which is not the same one as that which was used to produce the calibration readings originally. Accordingly, the prudent practice to follow is to always recheck the operability of the eddy current test equipment by confirming therewith the original calibration readings before the test equipment is employed in performing a surface examination of an actual component.

Assuming now that both the step of calibration has been performed whereby a series of calibration readings have been generated therefrom, and that the step of validating the operativeness of the eddy current test equipment has been performed, then in accordance with the method of the present invention the next step is to effect the actual surface examination of a given metal component. For purposes of describing this latter step, reference will be had by way of exemplification to the performance of a surface examination of a flywheel. Further, in this connection particular attention is directed to FIGS. 2 and 3 of the drawing. It is to be understood, however, that the method of the present invention is equally applicable for use for purposes of conducting surface examinations on other components such as various types of metal forgings, etc.

As best understood with reference to FIG. 2 of the drawing, for purposes of effecting a surface examination of a rotatable component, e.g., the flywheel denoted by the reference numeral 58 in FIG. 3, the eddy current probe 24 is preferably emplaced in the probe holder portion 32 of the probe holder and indexer means 30. The probe holder portion 32, as has been described hereinbefore in detail, is specifically designed so that the probe 24 is capable of being firmly positioned on a moving flywheel surface. In this regard, it is to be noted that the probe 24 is intended to be employed for purposes of effecting a surface examination of both the top and the sides of the flywheel 58. The probe holder portion 32 must also have the capability of moving freely over the multiplicity of bolt holes, some of which are seen at 60 in FIG. 3, with which the flywheel 58 is provided adjacent to its circumference.

The other portion of the probe holder and indexer means 30, i.e., the indexer portion 34, as has been described hereinbefore, is operative to enable a precision stepping or indexing of the probe 24 to take place over the surface of the flywheel 58. This indexing which is accomplished through the movement in controlled steps of the elongated member 40 is intended to duplicate the stepping which the probe 24 has previously undergone during the performance of the calibration step of the method and which gave rise to a series of calibration readings. For purposes of accomplishing the proper positioning of the probe 24 relative to the surface of the flywheel 58, the mounting plate 56 on which the probe holder and indexer means 30 is positioned is suitably located in fixed relation to a readily identifiable reference point on the flywheel 58. The manner in which the establishment of the location of the probe 24 relative to a known point on the surface of the flywheel 58 is effected using the mounting plate 56 is capable of being accomplished in many different ways. Preferably, however, the mounting plate 56 is fastened to the housing (not shown) within which the flywheel 58 is mounted for rotation.

With particular reference to FIG. 3 of the drawing, the manner in which the method of the present invention is practiced is as follows. A flywheel 58 bearing a coating of a corrosion resistant paint and having a plurality of bolt holes 60 formed along the circumference thereof is rotated so as to provide the motion required by the eddy current detection physics. The probe holder portion 32 and in particular the sled-like member 36 is positioned on the surface of the flywheel 58. The location of the sled-like member 36 relative to a particular known location on the surface of the flywheel 58 is established as a result of the securement of the mounting plate 56 to the housing (not shown) which surrounds the flywheel 58. After each rotation of the flywheel 58, the sled-like member 56 is indexed, i.e., stepped a preestablished distance radially of the surface of the flywheel 58. As the sled-like member 36 passes over the surface of the flywheel 58 the probe 24 produces eddy current signals which along with an indication of paint thicknesses are transmitted to a strip chart recorder schematically shown at 62 in FIG. 3 where in known fashion this information is recorded. In accord with the schematic representation of FIG. 3, there is shown at 64 an eddy current probe signal generator of known construction. In addition, a record is made on the strip chart recorder 62 of the location of the bolt holes 60. This is accomplished preferably through the use of a conventional photocell shown at 66 in FIG. 3 and amplifier means 68 whereby the signals produced by the photocell 66 indicating the presence of the bolt holes 60 are amplified and thereafter transmitted therefrom to the strip chart recorder 62 where they are recorded. This facilitates the subsequent location of recorded indications of defects detected in the surface of the flywheel 58. Other devices could be employed in lieu of the photocell 66 for this purpose such as a microswitch of conventional construction without departing from the essence of the invention. Finally, rather than effecting the indexing of the sled-like member 36 manually, i.e., by means of the handwheel 54 depicted in FIG. 2, automatic means may be utilized for this purpose without departing from the essence of the present invention. To this end, the screw thread 52 may be operatively connected to a suitable conventional form of motor as shown at 70 in phantom lines, in FIG. 3. Further, the motor 70 may be controlled through the use of a suitable conventional form of motor controller and microswitch shown in phantom lines at 72 and 74, respectively, in FIG. 3. In conclusion, as regards the matter of the recorded indications of defects in the surface of the flywheel 58, the nature and extent of these defects is determined from a comparison of the information recorded on the strip chart recorder 62 with that generated in the form of calibration readings during the performance of the calibration step of the method of the present invention.

Thus, in accordance with the present invention there has been provided a new and improved method for effecting a surface examination of a component. Moreover, the method of the present invention is particularly applicable for use for purposes of effecting surface examinations of coated metal components. In addition, in accord with the present invention a method is provided for effecting a surface examination of a coated metal component which does not necessitate the removal of the coating from the component for purposes of accomplishing the surface examination thereof. Further, the method of the present invention makes use of eddy current means for purposes of effecting a surface examination of a coated metal component. Additionally, in accordance with the present invention a method is provided which is capable of being used to effect from a surface examination of a coated metal component the detection of defects in accordance with the requirements established for such detection by existing governmental regulations. Also, the method of the present invention has achieved acceptance under the applicable industrial codes as a technique that is recognized for use for the performance of such surface examinations. Furthermore, in accord with the present invention a method for effecting a surface examination of a coated metal component which is relatively easy to employ, and which enables significant economies of time and manpower to be realized through the use thereof as compared to that required when utilizing prior art techniques.

While only one embodiment of our invention has been shown, it will be appreciated that modifications thereof, some of which have been alluded to hereinabove, may be readily made thereto by those skilled in the art. We, therefore, intend by the appended claims to cover the modifications which fall within the true spirit and scope of our invention.

What is claimed is:

1. A method for effecting a surface examination of a coated metal component to detect defects in the surface thereof without requiring that the coating be removed from the component for purposes of conducting the surface examination comprising the steps of:

a. providing a calibration block embodying characteristics similar to the component that is to undergo the surface examination and having a plurality of crack-like notches formed in a surface thereof, one of the plurality of crack-like notches embodying the same dimension as the minimal dimensioned crack desired to be detected in the component that is to undergo the surface examination;

b. providing a layer-like film of nonmetallic material embodying characteristics similar to the coating borne by the component that is to undergo the surface examination, the layer-like film of nonmetallic material comprises a plastic sheet-like member having a plurality of parallelly extending scribe lines provided thereon, the spacing between the adjoining ones of the multiplicity of scribe lines being such as to cause a reading to be provided of fifty percent of the value of the reading obtained from the minimal dimensioned crack-like notch when the eddy current means is moved along each of an adjoining pair of scribe lines;

c. positioning the plastic sheet-like member in superimposed relation on the calibration block so as to cover the plurality of crack-like notches formed in the calibration block;

d. establishing with eddy current means calibration readings from the calibration block having the plastic sheet-like member positioned in superimposed relation thereto;

e. performing a surface examination of the coated metal component with the eddy current means by moving the eddy current means over the surface of the coated metal component in a traversing pattern corresponding to the pattern defined by the plurality of scribe lines provided on the sheet-like member; and f. comparing the readings obtained from the surface examination of the coated metal component with the calibration readings obtained from the calibration block to establish the presence of any cracks of at least a minimal dimension in the surface of the coated metal component.

2. The method as set forth in claim 1 further including the step of validating the operativeness of the eddy current means preparatory to the step of performing the surface examination of the coated metal component.

3. The method as set forth in claim 2 wherein the coated metal component that undergoes the surface examination is a flywheel.

4. The method as set forth in claim 3 wherein the eddy current means includes a sled-like member that is positioned in engaging relation with the surface of the flywheel.

5. The method as set forth in claim 4 wherein in performing the surface examination with the eddy current means of the flywheel the eddy current means is manually indexed in a radial direction over the surface of the flywheel.

6. The method as set forth in claim 4 wherein in performing the surface examination with the eddy current means of the flywheel the eddy current means is automatically indexed in a radial direction over the surface of the flywheel.

* * * * *